(12) United States Patent
Kumar et al.

(10) Patent No.: US 11,842,799 B1
(45) Date of Patent: *Dec. 12, 2023

(54) SYSTEMS AND METHODS FOR MATCHING MASS SPECTROMETRY DATA WITH A PEPTIDE DATABASE

(71) Applicants: Sumesh Kumar, Miami, FL (US); Fahad Saeed, Miami, FL (US)

(72) Inventors: Sumesh Kumar, Miami, FL (US); Fahad Saeed, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,045

(22) Filed: Apr. 20, 2023

Related U.S. Application Data

(63) Continuation of application No. 17/815,814, filed on Jul. 28, 2022, now Pat. No. 11,798,654.

(51) Int. Cl.
| | |
|---|---|
| G01N 33/48 | (2006.01) |
| G01N 33/50 | (2006.01) |
| G16B 50/30 | (2019.01) |
| G16B 40/10 | (2019.01) |
| G01N 27/62 | (2021.01) |
| G06N 20/10 | (2019.01) |
| G01N 33/68 | (2006.01) |

(52) U.S. Cl.
CPC .......... *G16B 50/30* (2019.02); *G01N 27/62* (2013.01); *G06N 20/10* (2019.01); *G16B 40/10* (2019.02); *G01N 33/6848* (2013.01); *G06F 2212/454* (2013.01)

(58) Field of Classification Search
CPC ........ G16B 50/30; G16B 40/10; G06N 20/10; G01N 33/6848; G06F 2212/454
See application file for complete search history.

(56) References Cited

U.S. PATENT DOCUMENTS

| | | | |
|---|---|---|---|
| 2007/0156995 A1 | 7/2007 | Kaburlasos | |
| 2012/0036304 A1 | 2/2012 | Lais et al. | |
| 2014/0304462 A1* | 10/2014 | Venugopal | G06F 13/16 711/104 |

(Continued)

OTHER PUBLICATIONS

Moucheng Yang et al., A Complete CPU-FPGA Architecture for Protein Identification with Tandem Mass Spectrometry, 2019 International Conference on Field-Programmable Technology (ICFPT), IEEE, 2019, pp. 295-298, 4 pages.

(Continued)

*Primary Examiner* — Russell S Negin
(74) *Attorney, Agent, or Firm* — Saliwanchik, Lloyd & Eisenschenk

(57) ABSTRACT

Systems, architectures, devices, and methods for matching experimentally acquired mass spectrometry data with a peptide database are provided. The system architecture can include a host central processing unit (CPU) system, a bridge connecting the CPU system with a core control register (or registers), a plurality of processing elements (PEs), and a bus arbiter. The PEs can execute the computations in a parallel and asynchronous manner. The bus arbiter can be a first-come first-serve (FCFS)-based bus arbiter (i.e., can utilize an FCFS-based arbitration scheme).

20 Claims, 9 Drawing Sheets

(56) References Cited

U.S. PATENT DOCUMENTS

2015/0363345 A1  12/2015  Peng et al.
2016/0132442 A1  5/2016   Chiao
2020/0065206 A1  2/2020   Norrie et al.
2021/0037338 A1  2/2021   Scott et al.

OTHER PUBLICATIONS

Jin Qiu et al., FPGA Acceleration of the Scoring Process of X!TANDEM for Protein Identification, 27th International Conference on Field Programmable Logic and Applications (FPL), IEEE, 2017, 4 pages.

Eng et al., A fast SEQUEST cross correlation algorithm. Journal of Proteome Research, vol. 7, pp. 4598-4602. (Year: 2008).

Kong et al., MSFragger: ultrafast and comprehensive peptide identification in mass sepectrometry-based proteomics. Nature Methods, vol. 14, pp. 513-520. (Year: 2017).

Kumar et al., Communication-avoiding micro-architecture to compute Xcorr scores for peptide identification, 2021 31st International Conference on Field-Programmable Logic and Applications, Aug. 2021, pp. 99-103.

* cited by examiner

| Cache size | I/O time | Waiting time | Total communication time |
|---|---|---|---|
| 512B | 1.01s | 11.57s | 12.58s |
| 1kB | 0.52s | 5.19s | 5.71s |
| 2kB | 0.86ms | 2.2ms | 3.06ms |
| 4kB | 0.84ms | 2.1ms | 2.95ms |

FIG. 6

| Precursor mass Tolerance (Da) | Dot product operations | Crux | Hardware Accelerator | Relative Speed-up |
|---|---|---|---|---|
| 1.5 | 162.79M | 53.2s | 1.25s | 42 |
| 3 | 325.41M | 75s | 2.45s | 30 |
| 5 | 541.42M | 86s | 4.10s | 21 |
| 10 | 1.07B | 139s | 7.782s | 20 |
| 25 | 1.99B | 304s | 20.75s | 15 |
| 50 | 3.076B | 648s | 39.6s | 16 |

FIG. 7

SYSTEMS AND METHODS FOR MATCHING MASS SPECTROMETRY DATA WITH A PEPTIDE DATABASE

CROSS-REFERENCE TO RELATED APPLICATION

The present application is a continuation application of U.S. Application Ser. No. 17/815,814, filed Jul. 28, 2022, the disclosure of which is hereby incorporated by reference in its entirety, including all figures, tables, and drawings.

GOVERNMENT SUPPORT

This invention was made with government support under GM134384 awarded by the National Institute of Health. The government has certain rights in the invention.

BACKGROUND

Mass-spectrometry-based analysis is the preferred method for identification of proteins from complex biological samples. Recent developments in data acquisition and analysis techniques have enabled many powerful proteomic applications. Database search algorithms such as SEQUEST (see Eng et al., A fast sequest cross correlation algorithm, Journal of proteome research, 7(10):4598-4602, 2008), X!Tandem (see Craig et al., "TANDEM: matching proteins with tandem mass spectra.", Bioinformatics 20, no. 9, 1466-1467, 2004), and MSFragger (see Kong et al., Msfragger: ultrafast and comprehensive peptide identification in mass spectrometry-based proteomics, Nature methods, 14(5):513-520, 2017) can search high resolution mass-spectrometry data against an ever-increasing protein database to produce high quality matches. This has drastically increased the computation load for existing implementations of the database search algorithms.

BRIEF SUMMARY

Embodiments of the subject invention provide novel and advantageous systems, architectures, devices, and methods for matching experimentally acquired mass spectrometry data with a peptide database (e.g., computing a cross-correlation score). The system architecture can include a host central processing unit (CPU) system, a bridge connecting the CPU system with a core control register (or registers), a plurality of processing elements (PEs), and a bus arbiter. The PEs can execute the computations in a parallel and asynchronous manner. The bus arbiter can be a first-come first-serve (FCFS)-based bus arbiter (i.e., can utilize an FCFS-based arbitration scheme). The system architecture can further include a memory mapped bus connected to the bus arbiter and/or the bridge. An external memory interface can connect the memory mapped bus to one or more external memories (e.g., dynamic random access memory (DRAM), such as double data rate (DDR) DRAM). The system architecture can further include CPU memory. The bridge can be, for example, a peripheral component interconnect express (PCIe) direct memory access (DMA) bridge. Each PE can include an ion-matching kernel and/or local memory (e.g., random access memory (RAM) such as on-chip RAM).

In an embodiment, a system for matching experimentally acquired mass spectrometry data with a peptide database can comprise: a host CPU system; a core control register; a bridge connecting the host CPU system to the core control register; a plurality of PEs connected directly to the core control register and configured to execute, in parallel and asynchronously, computations related to matching the experimentally acquired mass spectrometry data with the peptide database; and a bus arbiter connected directly to the plurality of PEs. Each PE of the plurality of PEs can comprise local memory. Each PE of the plurality of PEs can further comprise an ion-matching kernel for computing dot product scores for matching the experimentally acquired mass spectrometry data with the peptide database. The bus arbiter can be an FCFS-based bus arbiter. The bridge can be a PCIe DMA bridge. The system can further comprise a memory mapped bus directly connected to the bus arbiter. The memory mapped bus can be directly connected to the bridge. The system can further comprise an external memory interface direction connected to the memory mapped bus and configured to connect the memory mapped bus to an external memory. The external memory can comprise DRAM. The local memory of each PE can be, for example, on-chip RAM. The on-chip RAM of each PE can have a cache size of at least 2 kilobytes (kB). Each PE of the plurality of PEs can further comprise a binary search module configured to fetch a candidate peptide and store it in a peptide first-in first-out (FIFO). The plurality of PEs can comprise any suitable number of PEs (e.g., 16 PEs or at least 16 PEs).

In another embodiment, a method for matching experimentally acquired mass spectrometry data with a peptide database can comprise: providing a system as described herein (the system comprising the memory mapped bus directly connected to the bus arbiter); receiving, by the host CPU, the experimentally acquired mass spectrometry data; sending the experimentally acquired mass spectrometry data, via the bridge, to the core control register; providing the experimentally acquired mass spectrometry data to the plurality of PEs, each PE of the plurality of PEs having the peptide database stored thereon; and performing, by the plurality of PEs in a parallel and asynchronous manner, computations to match the experimentally acquired mass spectrometry data with the peptide database, the performing of the computations comprising communicating with the memory mapped bus via the bus arbiter. The method can further comprise utilizing a wait counter register to keep track of a wait time of each PE of the plurality of PEs for access to the memory mapped bus, and the bus arbiter can grant access to a PE of the plurality of PEs with a highest wait time, such that the bus arbiter is a first-come first-serve (FCFS)-based bus arbiter. The bridge of the system can be a PCIe DMA bridge. The memory mapped bus of the system can be directly connected to the bridge of the system. The local memory of each PE of the system can be, for example, on-chip RAM. The on-chip RAM of each PE of the system can have a cache size of at least 2 kB. The method can further comprise, before providing the system, pre-sorting the peptide database. Each PE of the plurality of PEs of the system can further comprise a binary search module configured to fetch a candidate peptide and store it in a peptide FIFO.

BRIEF DESCRIPTION OF DRAWINGS

FIG. 6 shows a table of effect of cache size on average I/O and synchronization times while using 16 PEs.

FIG. 7 shows a table of run-time comparison of field-programmable gate array (FPGA) accelerator with Crux running on a 3.6 gigahertz (GHz) processor (Intel® I7-4790) using eight threads and 16 gigabytes (GB) of memory).

DETAILED DESCRIPTION

Figure 1:
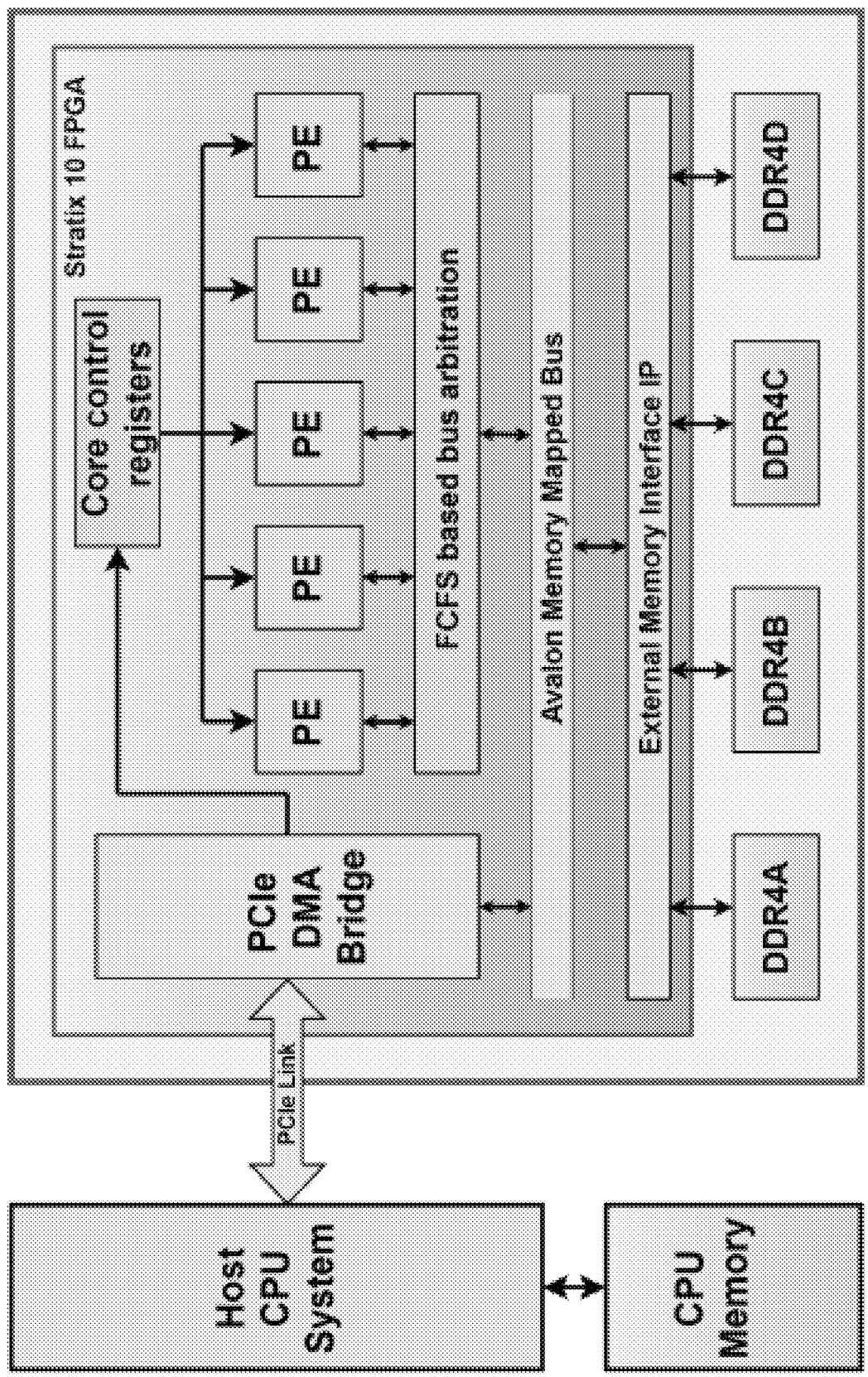
FIG. 1 shows a schematic view of a system architecture, according to an embodiment of the subject invention.

Embodiments of the subject invention provide novel and advantageous systems, architectures, devices, and methods for matching experimentally acquired mass spectrometry data with a peptide database (e.g., computing a cross-correlation score). The system architecture can include a host central processing unit (CPU) system, a bridge connecting the CPU system with a core control register (or registers), a plurality of processing elements (PEs), and a bus arbiter. The PEs can execute the computations in a parallel and asynchronous manner. The bus arbiter can be a first-come first-serve (FCFS)-based bus arbiter (i.e., can utilize an FCFS-based arbitration scheme). The system architecture can further include a memory mapped bus connected to the bus arbiter and/or the bridge. An external memory interface can connect the memory mapped bus to one or more external memories (e.g., dynamic random access memory (DRAM), such as double data rate (DDR) DRAM). The system architecture can further include CPU memory. The bridge can be, for example, a peripheral component interconnect express (PCIe) direct memory access (DMA) bridge. Each PE can include an ion-matching kernel and/or local memory (e.g., random access memory (RAM) such as on-chip RAM).

Cross-correlation (Xcorr) score is one of the most popular parameters for matching experimentally-acquired mass spectrometry data with a peptide database. The computed score is further used to identify proteins, which is a fundamental problem in the large-scale study of proteomes. A major challenge in computing Xcorr for large databases is to minimize the communication time of moving spectra across different hierarchies of memory. Embodiments of the subject invention can utilize an FPGA architecture that uses an adaptive caching approach to significantly minimize communication overhead (e.g., by 600 or more times).

FPGAs provide the opportunity to design customized hardware architectures optimized for any particular application. The architecture of embodiments can be based on parallel PEs that can execute the scoring task asynchronously and divide the entire search problem evenly among each other. The biggest challenge when using parallel processors is sharing a single memory bus, which can become a bottleneck if there are too many memory operations. Embodiments of the subject invention solve this problem by using an adaptive caching approach that adjusts the cache size according to the problem and reduces memory operations (e.g., by 600 or more times). A fairness-based bus arbitration module can also be used to reduce bus congestion.

The Xcorr computation problem involves four main steps: 1) read experimental spectra from main memory; 2) find candidate peptides for the copied spectrum; 3) generate a theoretical spectrum for each candidate peptide; and 4) compute modified cross-correlation between experimental spectrum and theoretical spectrum.

For the first step, a cache in the PE can be used to read and store the experimental spectrum. A cross-correlation score is required to be computed between the same experimental spectrum and every candidate peptide. If there is no cache or if the cache is not big enough to store the entire spectrum, a single spectrum can be read n times from the main memory if there are n candidate peptides. In order to solve this problem, adaptive caching can be used, where the cache size is selected to be big enough to store the biggest experimental spectrum vector found in the database.

For the second step a binary search element in FPGA can be used to search for the candidate peptide in log time. The search operation can be masked with a spectrum read operation to decrease or minimize the communication overhead.

For the third step, a simple shift array can be used along with a binary adder to generate every new theoretical ion in one clock cycle.

For the fourth step, a simple PE can be designed and used that matches ions between the theoretical spectrum and experimental spectrum. This PE can be replicated (e.g., 16 times) to compute multiple (e.g., 16) scores in parallel. The PE can work by reading an ion from the theoretical spectrum and matching it with a packet of the experimental spectrum. If it is matched then a new theoretical ion is read; if there is no match then a new packet of the experimental spectrum is read from cache until a match is found. This matching process can take as many cycles as there are packets in the experimental spectrum.

A major bottleneck in mass-spectrometry-based analysis is the cost of communication (i.e., cost of moving input and output data between different hierarchies of a system). Even though central processing units (CPUs) are operating at a much higher frequency, their performance gain for proteomics studies relies on efficiently utilizing system cache or some other input reuse technique to minimize the number of dynamic random access memory (DRAM) accesses. Consequently, the implementation of Crux (see McIlwain et al., Crux: rapid open source protein tandem mass spectrometry analysis, Journal of proteome research, 13(10):4488-4491, 2014; which is hereby incorporated by reference herein in its entirety), state-of-the-art software for computing Xcorr scores, utilizes processor registers to store peptide fragment ions to allow peptide reuse. While this allows one-side data reuse, the cost of accessing experimental spectra from main memory is not minimized as generally CPU registers are not large enough to hold the entire experimental spectrum. On the other hand, custom architectures using field programmable gate arrays (FPGAs) can achieve better performance for memory bound applications by utilizing the abundant on-chip RAM resources and custom-designed communication minimizing pipelines to allow experimental spectrum reuse (see also, Nurvitadhi et al., Accelerating recurrent neural networks in analytics servers: Comparison of fpga, cpu, gpu, and asic, In 2016 26th International Conference on Field Programmable Logic and Applications (FPL), pages 1-4, IEEE, 2016; which is hereby incorporated by reference herein in its entirety).

Embodiments of the subject invention provide communication-avoiding micro-architecture to accelerate the Xcorr score computation, which achieves two-side data reuse by utilizing local (e.g., on-chip) memory (e.g., RAM) to cache an entire experimental spectrum and a peptide broadcast bus to decrease the number of DRAM accesses. Experiments show that these optimizations result in a reduction of 600 times (600×) in the average number of DRAM accesses compared with a no-caching approach and a 24× increase in speed over Crux. Main contributions of embodiments of the subject invention include: a block RAM-based cache of size 2 kilobytes (kB) can be implemented to store experimental spectra and minimize redundant DRAM accesses; the peptide database can be pre-sorted, which allows the use of binary search to search candidate peptides, and the search operation need only be performed once per spectrum as the next peptide can be pre-fetched, hence achieving input locality; in order to allow input reuse, a peptide broadcast bus can be used to make it accessible to all the processing elements; an FCFS-based bus arbitration scheme can be implemented to minimize the synchronization time of processing elements sharing the system bus.

The Xcorr score between a theoretical spectrum vector X and an experimental spectrum vector Y of length n is defined as (see McCormack et al., An approach to correlate tandem mass spectral data of peptides with amino acid sequences in a protein database, Journal of the american society for mass spectrometry, 5(11):976-989,1994; which is hereby incorporated by reference herein in its entirety), $$X_{corr} = \sum_{i=0}^{n-1} X[i]Y[i] - \frac{1}{151}\sum_{i=0}^{n-1}\sum_{\tau=-75}^{\tau=75} X[i]Y[i-\tau] \qquad (1)$$

where τ is the amount by which vector is being serially shifted. However, SEQUEST implementation performs an optimization by pre-processing the experimental spectrum to perform dot product only once as summarized below (see Eng et al., A fast sequest cross correlation algorithm, Journal of proteome research, 7(10):4598-4602, 2008; which is hereby incorporated by reference herein in its entirety), $$Y_P = \sum_{i=0}^{n-1}\left(Y[i] - \frac{1}{151}\sum_{\tau=-75}^{\tau=75} Y[i-\tau]\right) \qquad (2)$$

Using (2) reduces the Xcorr computation to $$X_{corr} = \sum_{i=0}^{n-1} X[i]Y_P[i]$$

FIG. 1 shows an architectural setting of a heterogeneous computational system for Xcorr, according to an embodiment of the subject invention. Referring to FIG. 1, a host CPU can communicate with FPGA RAM via a bridge (e.g., a PCIe DMA bridge), which can be connected to a memory mapped bus (e.g., Intel® Avalon memory mapped bus). A core registers module can contain the computation parameters and can also be used for FPGA-CPU communication. In order to allow efficient use of the memory mapped bus, all processing elements (PEs) can be connected to a FCFS-based bus arbiter, which can in turn be connected to the memory mapped bus. Though FIG. 1 shows that the memory mapped bus is an Avalon memory mapped bus, this is for exemplary purposes only and should not be construed as limiting.

Figure 3:
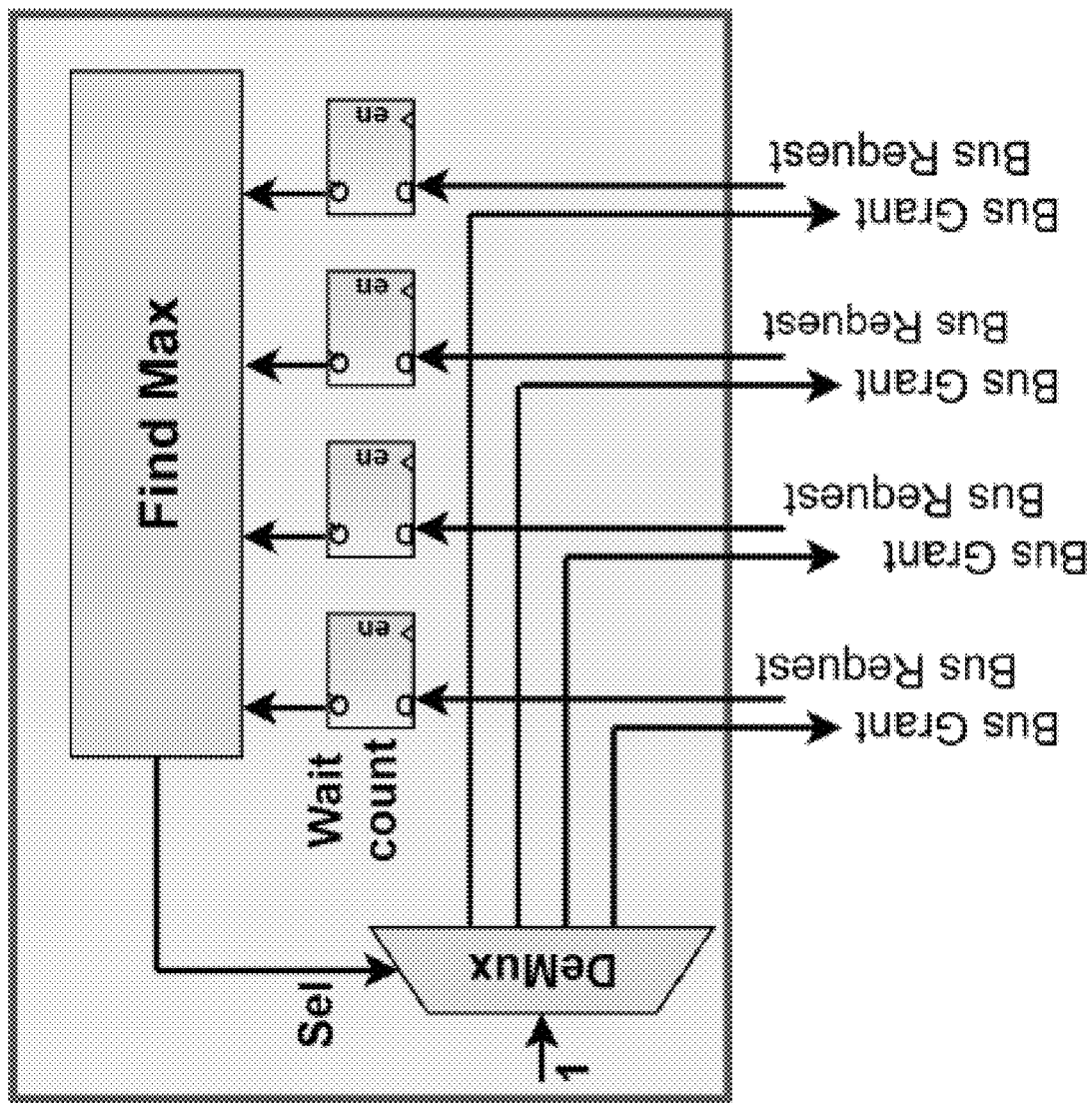
FIG. 3 shows a schematic view of a brief logic description of a bus arbitration module of a system architecture, according to an embodiment of the subject invention.

Referring still to FIG. 1, the host CPU can communicates (e.g., with PCIe DMA via a PCIe link) to transfer experimental spectra from host memory to FPGA memory. A set of directly accessible core control registers can hold computation parameters and control the operation. Each step of the algorithm can takes place inside each PE (i.e., reading experimental spectrum vectors one by one, searching for candidate peptides, generating theoretical spectrum, computing dot product scores, and writing the results back to main memory). The system can allow deployment of multiple PEs that execute the computations in a parallel and asynchronous manner. Because all the PEs share the same memory bus, an FCFS-based bus arbitration scheme can be implemented to achieve maximum bandwidth utilization. FIG. 3 shows a detailed view of the bus arbitration scheme.

Figure 2:
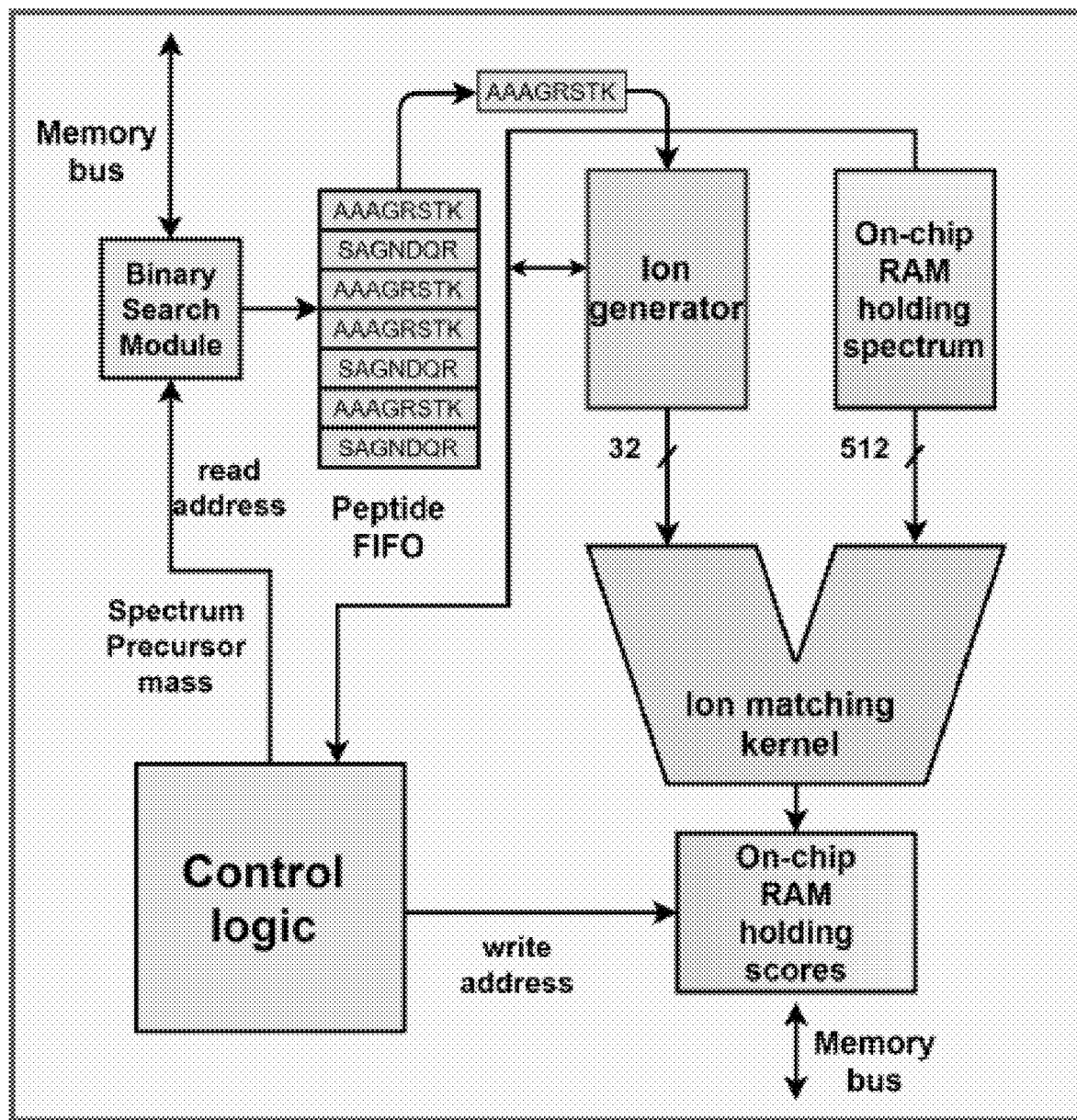
FIG. 2 shows a schematic view of detailed internal construction of a single processing element of a system architecture, according to an embodiment of the subject invention.

FIG. 2 shows detailed internal construction of a single PE. Referring to FIG. 2, at the heart of each PE is the controller (or control logic) that controls the function of all the sub-modules shown in FIG. 2. A binary search module can fetch a candidate peptide and store it in a peptide first in first out (FIFO). An ion generator can read the peptide and generate fragment ions. A packet (e.g., a 512 bit packet containing 16 32-bit ion m/z (where m is mass and z is charge number) and intensity pair values along with a 32-bit theoretical ion and intensity pair values) can be fed to the ion-matching kernel, which can find the matching peak and store the partial score in local (e.g., on-chip) memory (e.g., RAM). Each PE can take over the computation of a single spectrum with all the candidate peptides. The controller can determine the flow of computation, as shown in FIG. 2. The controller can copy an experimental spectrum in the form of m/z and ion intensity values from the external memory into local memory (e.g., on-chip RAM) and start the computation. Once the scores have been computed, they can be collected in the local memory and a request for bus access can be generated again to copy the scores into the DRAM.

FIG. 3 shows a brief logic description of the bus arbitration module. Referring to FIG. 3, bus request lines from all the PEs can come into the arbiter. When a PE is denied service, its wait count register can be incremented, dynamically increasing its priority for the next turn. The "Find Max" module is a comparator tree that finds which register(s) has/have the maximum value and grants access to the corresponding PE(s). In order to ensure load-balancing among the PEs, the bus arbitration module (or bus arbiter) can be utilized, and it is aimed to minimize total wait time for all the PEs. All the PEs requiring access to the bus connect with the "bus request" signal, which is connected to a wait counter register. The wait counter register keeps track of the wait time of every bus master so that the decision of contest for bus access is based on fairness (i.e., access is granted to a master that has been waiting for the longest time).

Figure 4:
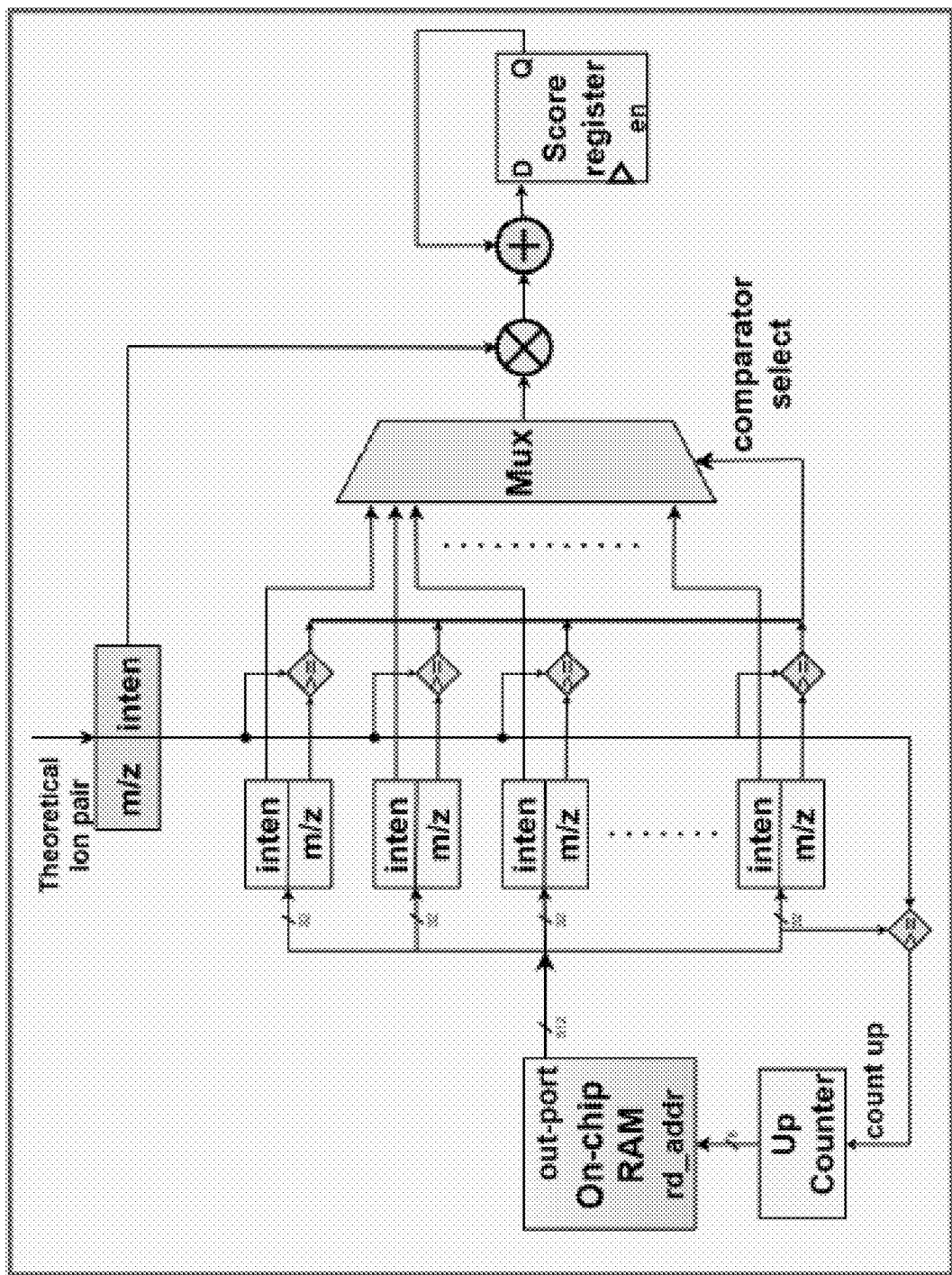
FIG. 4 shows a schematic view of an ion-matching circuit of a system architecture, according to an embodiment of the subject invention.

In order to compute the dot product scores between experimental spectra and a candidate peptide, the processing element can move a word (e.g., a 64-byte word) from the local memory (e.g., on-chip RAM) and a theoretically generated ion-pair from the candidate peptide to the peak-matching circuit. Each 64-byte word has 16 ion-pairs (using 16-bit floating point representation for intensity and 16 bit binary representation for m/z) from the experimental spectrum, which is stored in 16 32-bit registers inside the peak-matching circuit. The m/z value of the theoretical ion can be compared with all the experimental m/z values using a set of 16 parallel comparators as shown in FIG. 4, and the corresponding matching intensity value of the peak can be multiplied and accumulated in the output register. Once all the ions are traversed, the final Xcorr score can be sent to the local memory (e.g., on-chip RAM) and the process can repeat for the next candidate peptide.

FIG. 4 shows a view of the ion-matching circuit, which receives a 512 bit packet containing 16 experimental ions that are all compared with a theoretical ion in one cycle. The matched ions are multiplied and accumulated in the score register. If the theoretical ion is outside the range of current experimental ions, the next packet is requested from the local memory (e.g., on-chip RAM) by incrementing the counter.

Embodiments of the subject invention provide efficient communication-avoiding micro-architecture. Examples 1 and 2 herein demonstrate the applicability of the custom hardware design approach to accelerate crucial memory bound problems in mass-spectrometry-based omics. Optimizations for input reuse at all stages of the computation can be performed including cache implementation, pre-fetching, and input broadcasting. Although the system has been tested based on SEQUEST, this was done for exemplary purposes only, and it can be applied for other scoring techniques that involve dot product computation with little modification. The simulation results in Examples 1 and 2 suggest that the architecture is scalable for up to at least 32 PEs with linear speed-ups. The related art does not provide a design for computing Xcorr scores used in peptide deduction. Embodiments of the subject invention address this issue by providing an adaptive caching approach with FCFS bus arbitration.

Embodiments of the subject invention provide a focused technical solution to the focused technical problem of how to minimize the communication time of moving spectra across different hierarchies of memory in the case of mass-spectrometry-based analysis, as well as dealing with the bottleneck of a single memory bus when using parallel processors that share a single memory bus. Embodiments of the subject invention improve the computer system performing mass-spectrometry-based analysis (e.g., computing Xcorr) by providing a novel architecture that can decrease communication overhead (e.g., 600 times or more).

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

MATERIALS AND METHODS

The hardware used for experiments utilized Intel® Quartus Pro and Qsys system builder for Intel Stratix 10 FPGA. Very high speed integrated circuit (VHSIC) hardware description language (VHDL) was compiled using Quartus Pro to verify the maximum operable frequency of 200 megahertz (MHz). In order to evaluate the timing performance of the architecture, a cycle accurate simulator was implemented in Python that mimicked the exact timing response of the hardware. In the simulator, each sub-module was modeled as a class whose data objects represented the internal and external signals of the module and a clock-event( )method, which updated the signals whenever a clock edge occurred.

The PXD000612 dataset from the PRIDE database was used for the experiments, and this dataset contains 90,494 experimental spectra to score against a human proteome dataset containing 669,964 peptides. The experimental spectra were stored in the compressed sparse row (CSR) format with ion m/z value as the data index and ion intensity value as data element. Ion m/z values were stored in a 16 bit binary format and ion intensity values were represented using 16 bit half-precision floating point format.

EXAMPLE 1

Performance gains in the architecture of embodiments of the subject invention come from a combination of optimizations that minimize DRAM accesses and allow input reuse by using local memory (e.g., an on-chip RAM) as a local cache. In order to find the optimal cache size, experiments were performed for four different cache sizes along with the number of instantiated PEs in the design. The architecture used was as shown in FIGS. 1-4. The results of these experiments are presented in FIGS. 5A-5D.

Figure 5A:
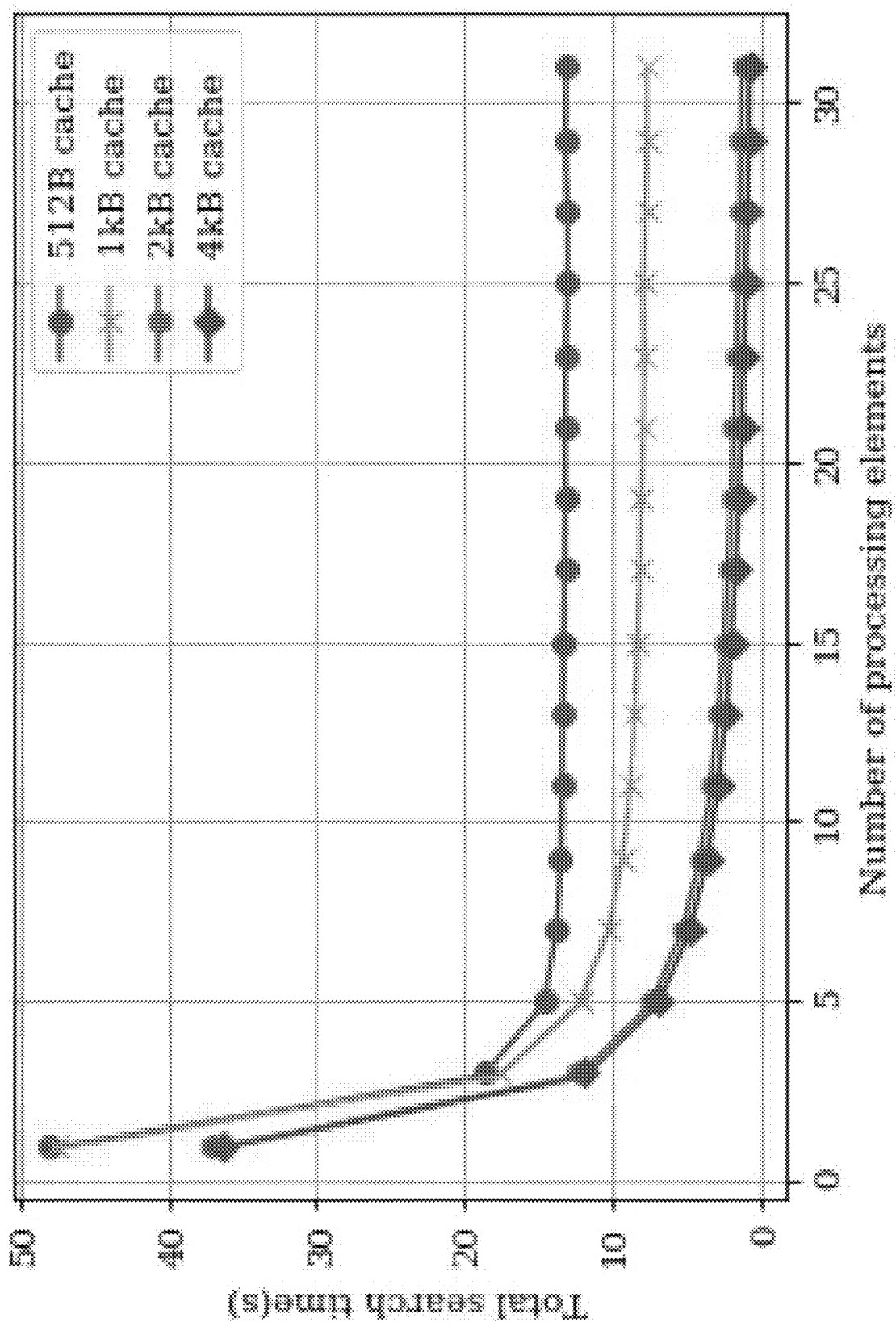
FIG. 5A shows a plot of total search time (in seconds (s)) versus number of instantiated processing elements (PEs) for cache size of 512 bytes (B), 1 kilobyte (kB), 2 kB, and 4 kB. The curve with the larger circular data points and the highest processing time at 32 PEs is for 512 B; the curve with the "X" data points is for 1 kB; the curve with the smaller circular data points and the second-lowest processing time at 20 PEs is for 2 kB; and the curve with the diamond data points and the lowest processing time at 20 PEs is for 4 kB. The search time decreases consistently with increasing number of PEs for cache size 2 kB and 4 kB but saturates for 512 B and 1 kB after six PEs due to increased memory requests.

The performance of the architecture was analyzed by elaborating the total processing time spent on computation and communication. In order to understand the effect of cache size, the communication time was further divided in terms of input/output (I/O) and waiting time. Average computation time was defined as average time each PE spends on computing dot product; average I/O time was defined as average time spent by each PE on DRAM read/write operations; and average waiting time was defined as average time each PE spends on waiting to get access to the system bus. The total processing time for dot product computations is shown in FIG. 5A, and it is evident that increasing the number of PEs from 1 to 31 displayed significant speed increase up until 15 PEs for a cache size of 2 kilobytes (kB) and 4 kB, while for cache size below 2 kB the speed increase plateaued after six PEs.

Figure 5B:
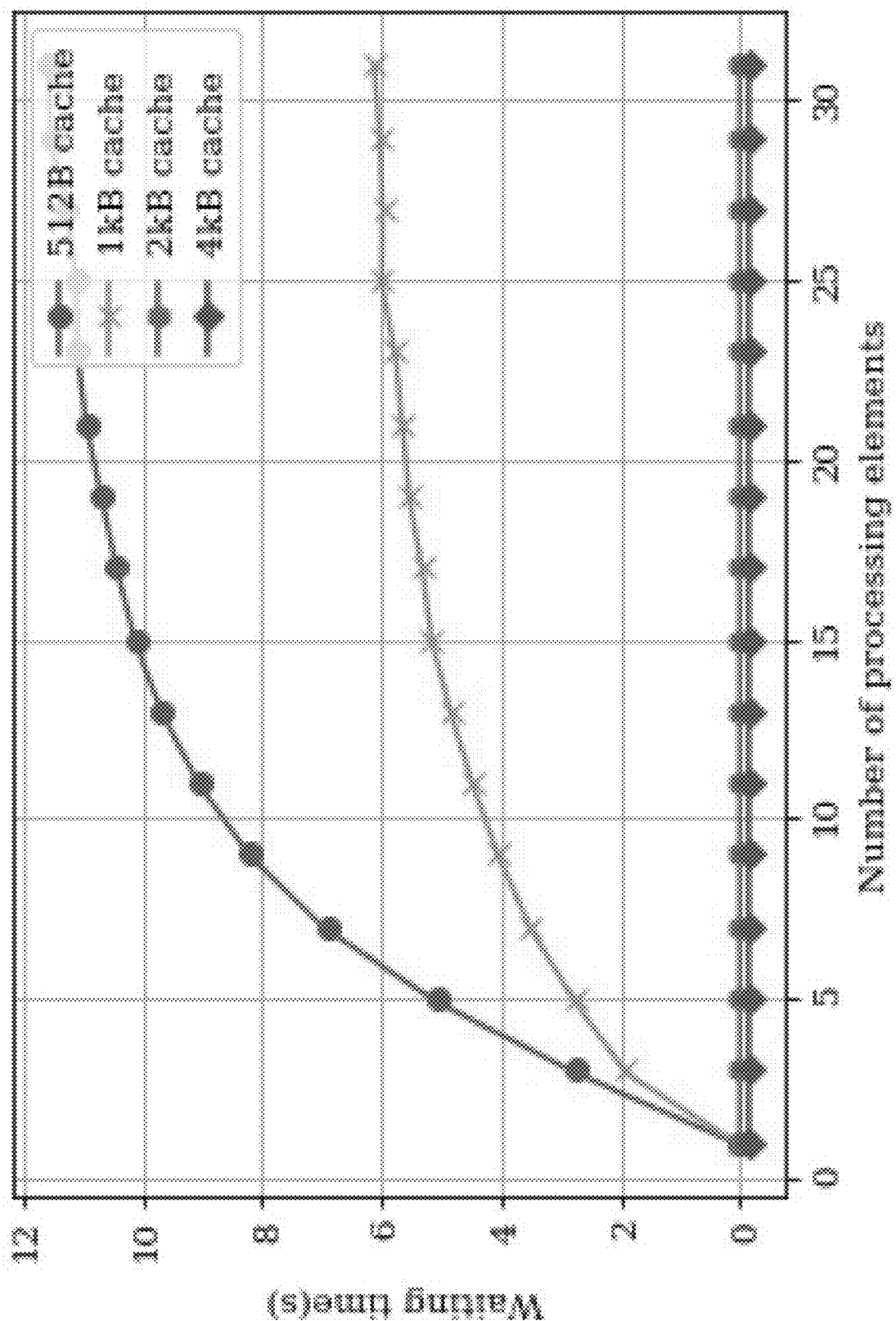
FIG. 5B shows a plot of waiting time (or average synchronization time) (in s) versus number of PEs for cache size of 512 B, 1 kB, 2 kB, and 4 kB. The curve with the larger circular data points and the highest waiting time at 20 PEs is for 512 B; the curve with the "X" data points is for 1 kB; the curve with the smaller circular data points and the second-lowest waiting time at 20 PEs is for 2 kB; and the curve with the diamond data points and the lowest waiting time at 20 PEs is for 4 kB. The waiting time is the time spent by PEs waiting for memory bus access. The wait time increases exponentially for cache size below 2 kB.
Figure 5C:
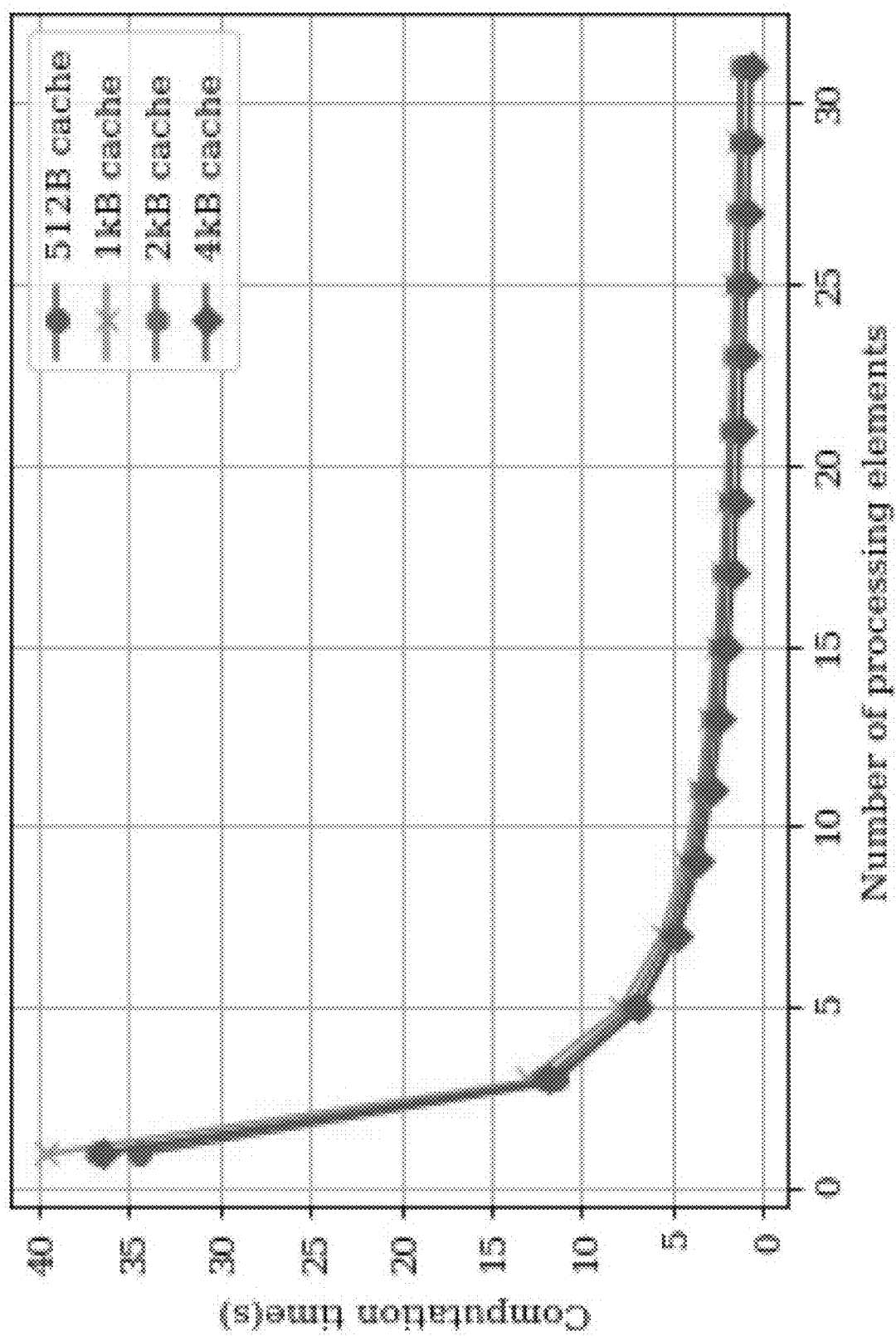
FIG. 5C shows a plot of average computation time (in s) versus number of PEs for cache size of 512 B, 1 kB, 2 kB, and 4 kB. The curve with the larger circular data points is for 512 B; the curve with the "X" data points is for 1 kB; the curve with the smaller circular data points is for 2 kB; and the curve with the diamond data points is for 4 kB. The computation time is the time spent on actual computation, which decreases with the increasing number of PEs but is not affected by cache size.
Figure 5D:
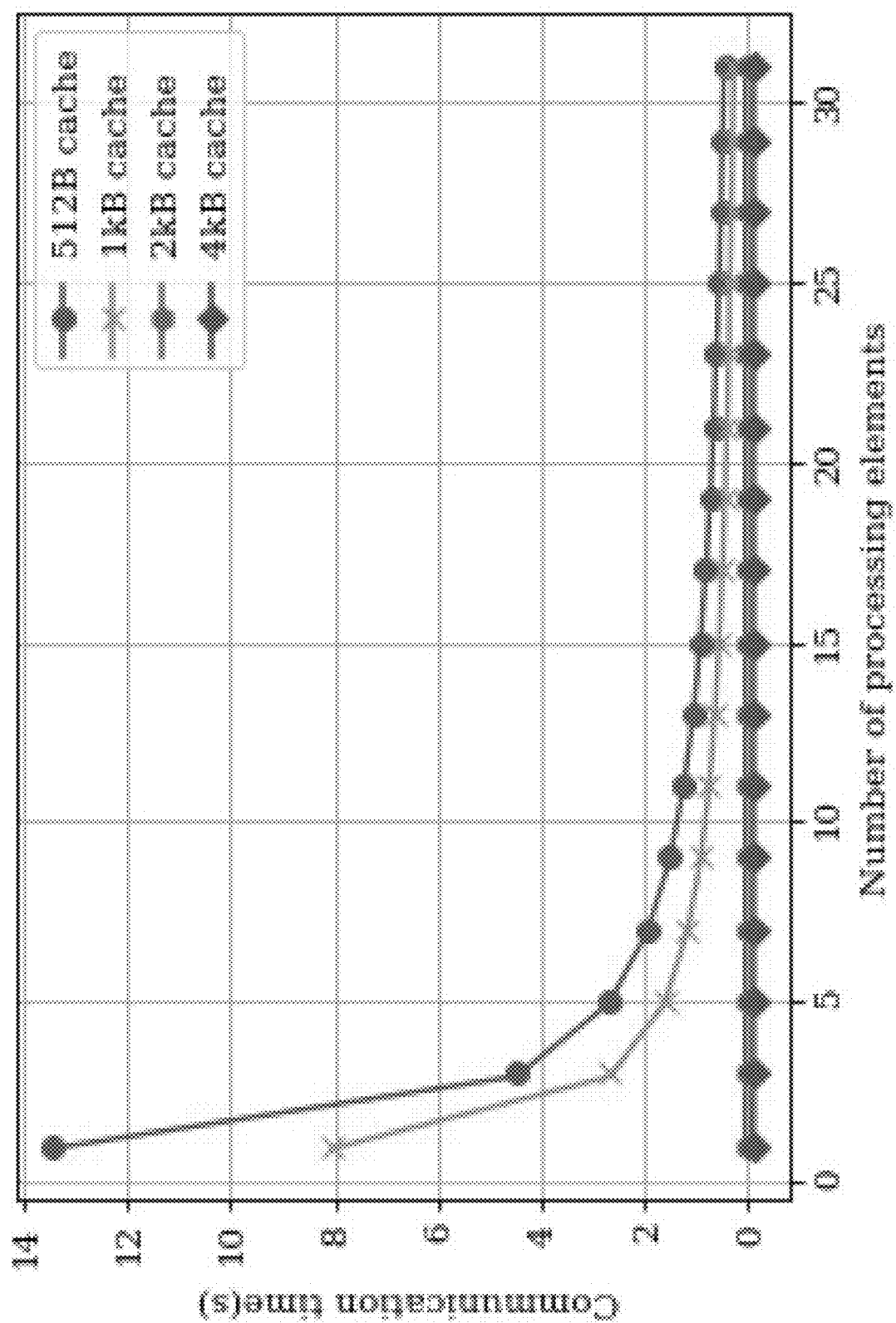
FIG. 5D shows a plot of communication time (in s) versus number of PEs for cache size of 512 B, 1 kB, 2 kB, and 4 kB. The curve with the larger circular data points and the highest processing time at 5 PEs is for 512 B; the curve with the "X" data points is for 1 kB; the curve with the smaller circular data points and the second-lowest processing time at 5 PEs is for 2 kB; and the curve with the diamond data points and the lowest processing time at 5 PEs is for 4 kB. The communication time is average input/output (I/O) time per PE, and it is higher for cache size below 2 kB. Though, there is little difference in performance between 2 kB and 4 kB.

FIGS. 5B, 5C, and 5D show the breakdown of the total processing time in terms of computation, I/O, and waiting time for a single PE, respectively. FIG. 5B shows that waiting time is zero for 1 PE as the memory bus is not being shared. As the number of PEs increases, there is an almost exponential increase in the average waiting time of a PE for cache sizes below 2 kB. The waiting times for 2 kB and 4 kB cache stay constant even when 31 PEs are instantiated. The average computation time per PE is not impacted by the size of cache, but it decreases sharply when the number of PEs increases to 11. FIG. 5D shows that the total I/O time (i.e., total number of DRAM accesses) is orders of magnitude greater for cache size below 2 kB. The table in FIG. 6 further illustrates that increasing cache size from 1 kB to 2 kB results in a 600-time reduction in the average I/O time.

Based on the results of the experiments, the architecture can include 16 instantiated PEs to achieve efficient (possibly maximum) performance from the system.

EXAMPLE 2

The total search time of the architecture from Example 1 was compared with Crux for six different values of precursor mass window. The table in FIG. 7 presents the total run-time of Crux running on a 3.6 gigahertz (GHz) Intel® 17-4970 processor with 16 gigabytes (GB) of system memory, as well as the run-time of the hardware accelerator of embodiments of the subject invention (with the architecture from Example 1) running at a 200 MHz clock frequency (in the column labeled "Hardware Accelerator"). Referring to FIG. 7, it can be seen that the hardware accelerator of embodiments of the subject invention increased the speed from 15 to 42 times over Crux for the six different values of precursor mass window tested.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for matching experimentally acquired mass spectrometry data with a peptide database, the system comprising:
   a host central processing unit (CPU) system;
   a core control register;
   a bridge connecting the host CPU system to the core control register;
   a plurality of processing elements (PEs) connected directly to the core control register and configured to execute, in parallel and asynchronously, computations related to matching the experimentally acquired mass spectrometry data with the peptide database; and
   a bus arbiter connected directly to the plurality of PEs, each PE of the plurality of PEs comprising local memory, each PE of the plurality of PEs further comprising an ion-matching kernel for computing dot product scores for matching the experimentally acquired mass spectrometry data with the peptide database, and
   the system being configured to perform adaptive caching.

2. The system according to claim 1, the bus arbiter being a first-come first-serve (FCFS)-based bus arbiter.

3. The system according to claim 1, the bridge being a peripheral component interconnect express (PCIe) direct memory access (DMA) bridge.

4. The system according to claim 1, further comprising a memory mapped bus directly connected to the bus arbiter.

5. The system according to claim 4, the memory mapped bus being directly connected to the bridge.

6. The system according to claim 4, further comprising an external memory interface directly connected to the memory mapped bus and configured to connect the memory mapped bus to an external memory.

7. The system according to claim 6, the external memory comprising dynamic random access memory (DRAM).

8. The system according to claim 6, each PE of the plurality of PEs further comprising a control logic configured to determine a flow of computation within the respective PE.

9. The system according to claim 8, the control logic of each PE of the plurality of PEs being further configured to copy an experimental spectrum from the external memory into the local memory of the respective PE.

10. The system according to claim 8, the on-chip RAM of each PE having a cache size of at least 2 kilobytes (kB).

11. The system according to claim 1, the local memory of each PE being on- chip random access memory (RAM).

12. The system according to claim 1, each PE of the plurality of PEs further comprising a binary search module configured to fetch a candidate peptide and store it in a peptide first-in first-out (FIFO).

13. The system according to claim 1, the plurality of PEs comprising 16 PEs.

14. The system according to claim 1, the plurality of PEs comprising at least 16 PEs.

15. The system according to claim 1, each PE of the plurality of PEs further comprising a control logic configured to determine a flow of computation within the respective PE.

16. A system for matching experimentally acquired mass spectrometry data with a peptide database, the system comprising:
   a host central processing unit (CPU) system;
   a core control register;
   a bridge connecting the host CPU system to the core control register;
   a plurality of processing elements (PEs) connected directly to the core control register and configured to execute, in parallel and asynchronously, computations related to matching the experimentally acquired mass spectrometry data with the peptide database;
   a bus arbiter connected directly to the plurality of PEs;
   a memory mapped bus directly connected to the bus arbiter and to the bridge; and
   an external memory interface directly connected to the memory mapped bus and configured to connect the memory mapped bus to an external memory,
   each PE of the plurality of PEs comprising local memory,
   each PE of the plurality of PEs further comprising an ion-matching kernel for computing dot product scores for matching the experimentally acquired mass spectrometry data with the peptide database,
   each PE of the plurality of PEs further comprising a binary search module configured to fetch a candidate peptide and store it in a peptide first-in first-out (FIFO),
   the local memory of each PE being on-chip random access memory (RAM),
   the on-chip RAM of each PE having a cache size of at least 2 kilobytes (kB),
   the bus arbiter being a first-come first-serve (FCFS)-based bus arbiter,
   the bridge being a peripheral component interconnect express (PCIe) direct memory access (DMA) bridge,
   the external memory comprising dynamic random access memory (DRAM),
   the plurality of PEs comprising at least 16 PEs, and
   the system being configured to perform adaptive caching.

17. The system according to claim 16, each PE of the plurality of PEs further comprising a control logic configured to determine a flow of computation within the respective PE.

18. The system according to claim 17, the control logic of each PE of the plurality of PEs being further configured to copy an experimental spectrum from the external memory into the local memory of the respective PE.

19. The system according to claim 16, each PE of the plurality of PEs further comprising a control logic configured to copy an experimental spectrum from the external memory into the local memory of the respective PE.

20. The system according to claim 16, the plurality of PEs comprising exactly 16 PEs.

* * * * *